US010452982B2

(12) United States Patent
Ichiboshi et al.

(10) Patent No.: US 10,452,982 B2
(45) Date of Patent: Oct. 22, 2019

(54) EMOTION ESTIMATING SYSTEM

(71) Applicant: FUJI XEROX CO., LTD., Tokyo (JP)

(72) Inventors: Akira Ichiboshi, Kanagawa (JP);
Roshan Thapliya, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 183 days.

(21) Appl. No.: 15/583,098

(22) Filed: May 1, 2017

(65) Prior Publication Data

US 2018/0114125 A1 Apr. 26, 2018

(30) Foreign Application Priority Data

Oct. 24, 2016 (JP) ................. 2016-207696

(51) Int. Cl.
*G06N 5/04* (2006.01)
*G06N 20/00* (2019.01)
*G10L 25/63* (2013.01)
*A61B 5/00* (2006.01)
*A61B 5/0205* (2006.01)
(Continued)

(52) U.S. Cl.
CPC ............. *G06N 5/04* (2013.01); *A61B 5/0077* (2013.01); *A61B 5/0205* (2013.01); *A61B 5/1113* (2013.01); *A61B 5/165* (2013.01); *A61B 5/4803* (2013.01); *A61B 5/7267* (2013.01); *A61B 5/741* (2013.01); *A61B 7/04* (2013.01); *B25J 11/0005* (2013.01); *G06N 3/008* (2013.01);
(Continued)

(58) Field of Classification Search
CPC ........ G06N 5/04; G06N 3/008; G06N 99/005; A61B 5/165; A61B 5/4803; A61B 5/7267; A61B 7/04; A61B 5/0077; A61B 5/0205; A61B 5/1113; A61B 5/741; A61B 5/024; A61B 5/0531; B25J 11/0005; G10L 25/63
USPC ................................... 700/245, 246
See application file for complete search history.

(56) References Cited

U.S. PATENT DOCUMENTS 6,934,604 B1 * 8/2005 Sabe ...................... G06N 3/008
700/245
7,065,490 B1 * 6/2006 Asano .................. G10L 13/033
318/568.12
(Continued)

FOREIGN PATENT DOCUMENTS

JP 2006-071936 A 3/2006
JP 2012-059107 A 3/2012

OTHER PUBLICATIONS

Han et al., A Design for Smooth Transition of Robotic Emotional States, 2010 IEEE Workshop on Advanced Robotics and its Social Impacts (ARSO), pp. 13-18. (Year: 2010).*
(Continued)

*Primary Examiner* — Jaime Figueroa
(74) *Attorney, Agent, or Firm* — Oliff PLC

(57) ABSTRACT

An emotion estimating system includes a learning model and an estimation unit. The learning model accepts external information and biological information as input, and outputs an emotion of a user. The estimation unit changes a weighting applied to external information about the user detected by a first detector and a weighting applied to biological information about the user detected by a second detector in accordance with a situation around the user, and estimates the emotion output as a result of inputting external infor-
(Continued)

mation and biological information changed by the respective weightings into the learning model as the emotion of the user.

14 Claims, 11 Drawing Sheets

(51) Int. Cl.
    *A61B 5/11*     (2006.01)
    *A61B 5/16*     (2006.01)
    *A61B 7/04*     (2006.01)
    *B25J 11/00*     (2006.01)
    *G06N 3/00*     (2006.01)
    *A61B 5/024*     (2006.01)
    *A61B 5/053*     (2006.01)

(52) U.S. Cl.
    CPC .............. *G06N 20/00* (2019.01); *G10L 25/63* (2013.01); *A61B 5/024* (2013.01); *A61B 5/0531* (2013.01)

(56) References Cited

U.S. PATENT DOCUMENTS

| | | | | |
|---|---|---|---|---|
| 7,113,848 | B2* | 9/2006 | Hanson | G06N 3/008 521/79 |
| 9,079,313 | B2* | 7/2015 | Olivier, III | B25J 9/1689 |
| 10,144,135 | B2* | 12/2018 | Le Borgne | B25J 9/1694 |
| 2002/0156751 | A1* | 10/2002 | Takagi | G06N 3/008 706/12 |
| 2002/0161480 | A1* | 10/2002 | Kakutani | G06N 3/008 700/245 |
| 2003/0067486 | A1* | 4/2003 | Lee | G06N 3/004 715/751 |
| 2007/0074114 | A1* | 3/2007 | Adjali | G06F 3/01 715/706 |
| 2008/0050999 | A1* | 2/2008 | Jang | A63H 3/365 446/337 |
| 2008/0077277 | A1* | 3/2008 | Park | G06N 3/008 700/245 |
| 2010/0046806 | A1* | 2/2010 | Baughman | G06F 21/316 382/115 |
| 2011/0144804 | A1* | 6/2011 | Song | G06N 3/006 700/246 |
| 2014/0223462 | A1* | 8/2014 | Aimone | A61B 5/0476 725/10 |
| 2017/0239812 | A1* | 8/2017 | Thapliya | B25J 9/163 |
| 2017/0266812 | A1* | 9/2017 | Thapliya | B25J 9/0003 |
| 2018/0077095 | A1* | 3/2018 | Deyle | H04L 51/10 |

OTHER PUBLICATIONS

Lee et al., A General Behavior Generation Module for Emotional Robots Using Unit Behavior Combination Method, 2009,The 18th IEEE International Symposium on Robot and Human Interactive Communication,Toyama, Japan, Sep. 27-Oct. 2, 2009, pp. 375-380. (Year: 2009).*

Han et al., A New Information Fusion Method for Bimodal Robotic Emotion Recognition, 2008, Journal of Computers, vol. 3, No. 7, Jul. 2008, pp. 39-47. (Year: 2008).*

Park et al., An Emotion Expression System for the Emotional Robot, 2007, IEEE International Symposium on Consumer Electronics , 2007. ISCE 2007, pp. 1-6. (Year: 2007).*

Han et al., Autonomous Emotional Expression Generation of a Robotic Face, 2009, Proceedings of the 2009 IEEE International Conference on Systems, Man, and Cybernetics, San Antonio, TX, USA—Oct. 2009, pp. 2427-2432. (Year: 2009).*

Breazeal, Cynthia, Emotion and sociable humanoid robots, 2003, International Journal of Human-Computer Studies 59 (2003), pp. 119-155. (Year: 2003).*

Park et al., Emotion Expression and Environment Through Affective Interaction, Proceedings of the 17th World Congress The International Federation of Automatic Control, Seoul, Korea, Jul. 6-11, 2008, pp. 12691-12696. (Year: 2008).*

Lee et al., Development of an Android for Emotional Expression and Human Interaction, 2008, Proceedings of the 17th World Congress The International Federation of Automatic Control Seoul, Korea, Jul. 6-11, 2008, pp. 4336-4337. (Year: 2008).*

* cited by examiner

EMOTION ESTIMATING SYSTEM

CROSS-REFERENCE TO RELATED APPLICATIONS

This application is based on and claims priority under 35 USC 119 from Japanese Patent Application No. 2016-207696 filed Oct. 24, 2016.

BACKGROUND

Technical Field

The present invention relates to an emotion estimating system.

SUMMARY

According to an aspect of the invention, there is provided an emotion estimating system including a learning model and an estimation unit. The learning model accepts external information and biological information as input, and outputs an emotion of a user. The estimation unit changes a weighting applied to external information about the user detected by a first detector and a weighting applied to biological information about the user detected by a second detector in accordance with a situation around the user, and estimates the emotion output as a result of inputting external information and biological information changed by the respective weightings into the learning model as the emotion of the user.

BRIEF DESCRIPTION OF THE DRAWINGS

An exemplary embodiment of the present invention will be described in detail based on the following figures, wherein.

DETAILED DESCRIPTION

Figure 1:
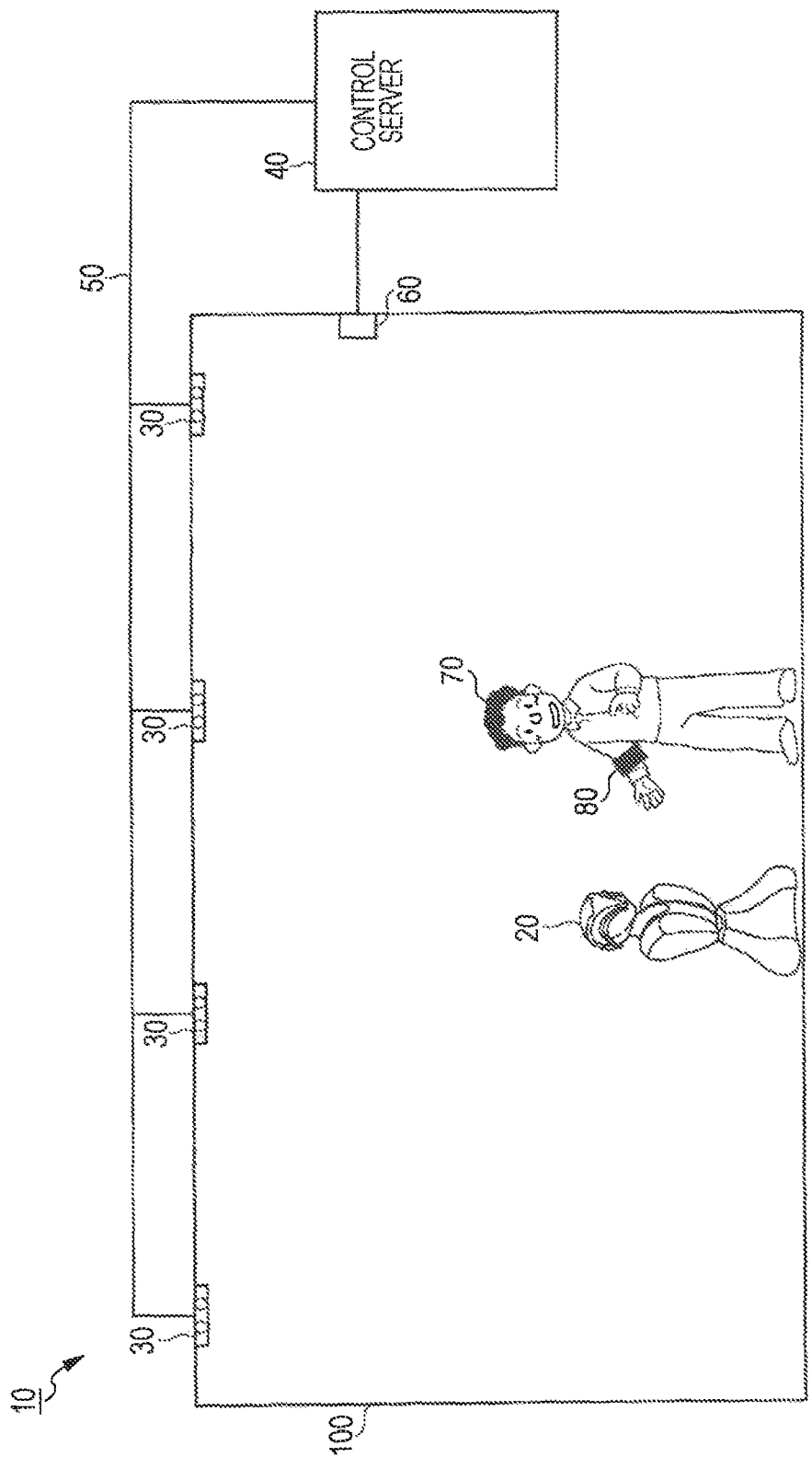
FIG. 1 is an explanatory diagram illustrating an example of an emotion estimating system 10 according to an exemplary embodiment of the present invention.

An emotion estimating system 10 according to an exemplary embodiment of the present invention will be described with reference to FIG. 1. The emotion estimating system 10 according to the present exemplary embodiment is provided with an interactive robot 20 placed in a certain, comparatively large area such as a floor of an office building (hereinafter called the workplace) 100, multiple environmental sensors 30 placed on the ceiling and walls of the workplace 100, and a control server 40. The control server 40 is connected to the interactive robot 20 and the environmental sensors 30 by a network 50. Particularly, the control server 40 and the interactive robot 20 are connected wirelessly via an access point 60 placed on a wall or the like of the workplace 100. Furthermore, a user 70 is present in the workplace 100, a biosensor 80 is attached to the wrist or arm of the user 70, and the biosensor 80 and the control server 40 are connected wirelessly via the access point 60.

The environmental sensors 30 detect external information such as the expression, posture, and complexion of the user 70, and additionally detect information about the situation of the user 70. The situation of the user 70 includes, for example, whether the user 70 is sitting, standing, participating in a conference, or engaged in conversation. Also, the information detected by the environmental sensors 30 also includes information by which to infer who the user 70 is.

The biosensor 80 is worn on the wrist or arm of the user 70, and detects biological information about the user 70. The biological information includes data related to the skin resistance, heart rate, and body temperature of the user 70, for example. The information related to the skin resistance includes not only the current skin resistance value, but also data about the change in the skin resistance value compared to normal, and the variation in the skin resistance value per unit time. Similarly, the information related to the heart rate includes not only the current heart rate, but also data about the change in the heart rate compared to normal, and the variation in the heart rate per unit time. Also, the data related to the body temperature includes, in addition to the current body temperature, the change in the body temperature compared to normal, and the change in the body temperature per unit time.

Figure 2:
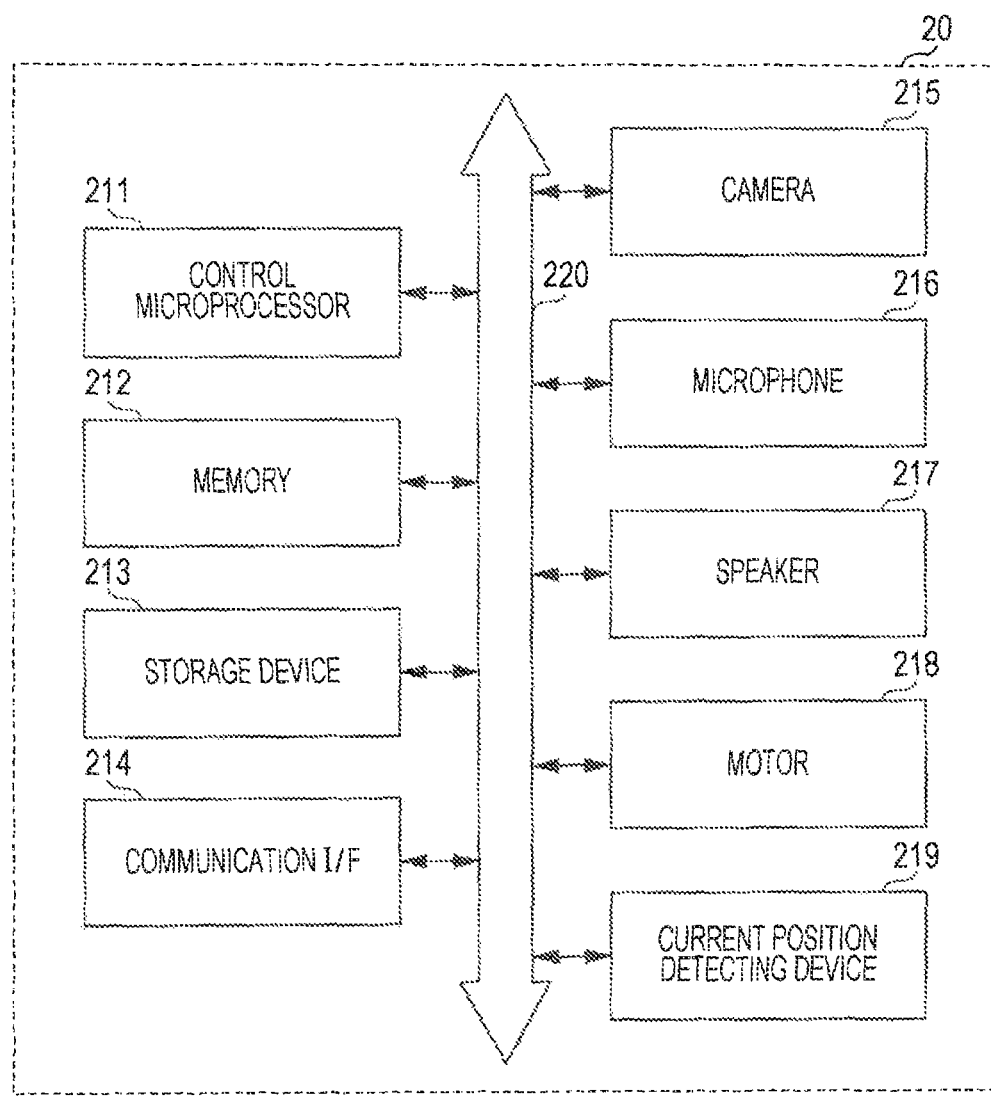
FIG. 2 is a hardware configuration diagram of an interactive robot 20 according to an exemplary embodiment.

First, the interactive robot 20 according to the present exemplary embodiment will be described with reference to FIGS. 2 and 3. FIG. 2 is a hardware configuration diagram of the interactive robot 20. As illustrated in FIG. 2, the interactive robot 20 is provided with a control microprocessor 211, memory 212, a storage device 213 such as a hard disk drive (HDD) or a solid-state drive (SSD), a communication interface 214, a camera 215, a microphone 216, a speaker 217, a motor 218, and a current position detecting device 219, which are respectively connected to a control bus 220.

The control microprocessor 211 centrally controls the operation of each component of the interactive robot 20 on the basis of a control program stored in the storage device 213. The memory 212 temporarily stores data such as the speech of a dialogue when the interactive robot 20 interacts with a user, the dialogue content, and an image of the expression, behavior, and body state of a user 50 captured by the camera 215. The storage device 213 stores a control program for controlling each component of the interactive robot 20. The communication interface 214 conducts communication control by which the interactive robot 20 communicates with the control server 40 via the access point 60.

The camera 215 captures, and stores in the memory 212, changes in the user's expression, behavior, body state, and the like. When the interactive robot 20 interacts with a user, the user's speech is detected and stored in the memory 212, or in other words recorded, by the microphone 216. Instead of recording the speech directly, the dialogue content after interpreting the speech content, as well as the pitch and speed of the words may be stored in the memory 212. The speaker 217 outputs speech generated by a dialogue control unit discussed later of the interactive robot 20. The motor 218 causes the interactive robot 20 to move to a certain position on the basis of movement control information generated in a movement control unit discussed later. The current position detecting device 219 includes components such as an acceleration sensor, a GPS signal reception device, or a position information signal reception device. The current position detecting device 219 specifies the current position of the interactive robot 20, and temporarily stores the current position in the memory 212.

Figure 3:
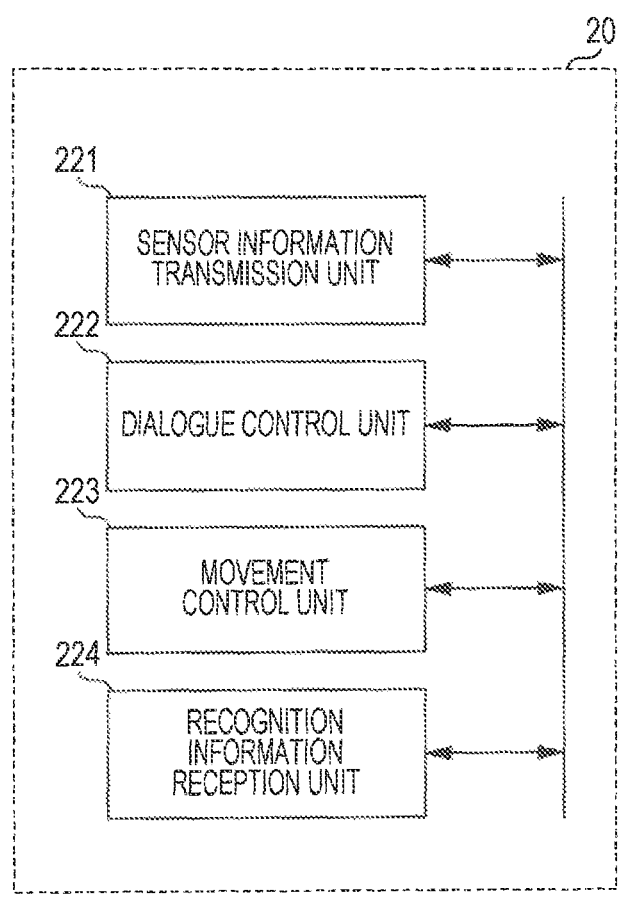
FIG. 3 is a function block diagram of an interactive robot 20 according to an exemplary embodiment.

FIG. 3 is a function block diagram of the interactive robot 20. By having the control microprocessor 211 execute a control program stored in the storage device 213, the interactive robot 20 functions as a sensor information transmission unit 221, a dialogue control unit 222, a movement control unit 223, and a recognition information reception unit 224, as illustrated in FIG. 3.

The sensor information transmission unit 221 transmits, to the control server 40, external information about the user 70 detected by the camera 215 and the microphone 216 of the interactive robot 20. External information includes data about the expression and behavior of the user 70 captured by the camera 215, and data about the pitch and speed of the words spoken by the user 70 detected by the microphone 216.

The dialogue control unit 222 controls dialogue that the interactive robot 20 conducts with the user 70, and also generates the content of responses to the user. For example, the dialogue control unit 222 generates a response message according to dialogue content stored in the memory 212, and outputs the generated response message to the speaker 217. At this time, the dialogue control unit 222 adjusts the volume and speed of the output speech of the message according to an emotion of the user 70 received by the recognition information reception unit 224 discussed later.

The movement control unit 223 controls the movement of the interactive robot 20. When the position of the user 70 is known, and there is a movement instruction from the control server 40, the movement control unit 223 generates movement control information by which to move from the current position to a destination position, controls the operation of the motor 218 while referring to information about the current position detected by the current position detecting device 219, and thereby causes the interactive robot 20 to move.

The recognition information reception unit 224 receives an emotion of the user 70 estimated by the control server 40, and temporarily stores the emotion in the memory 212.

Figure 4:
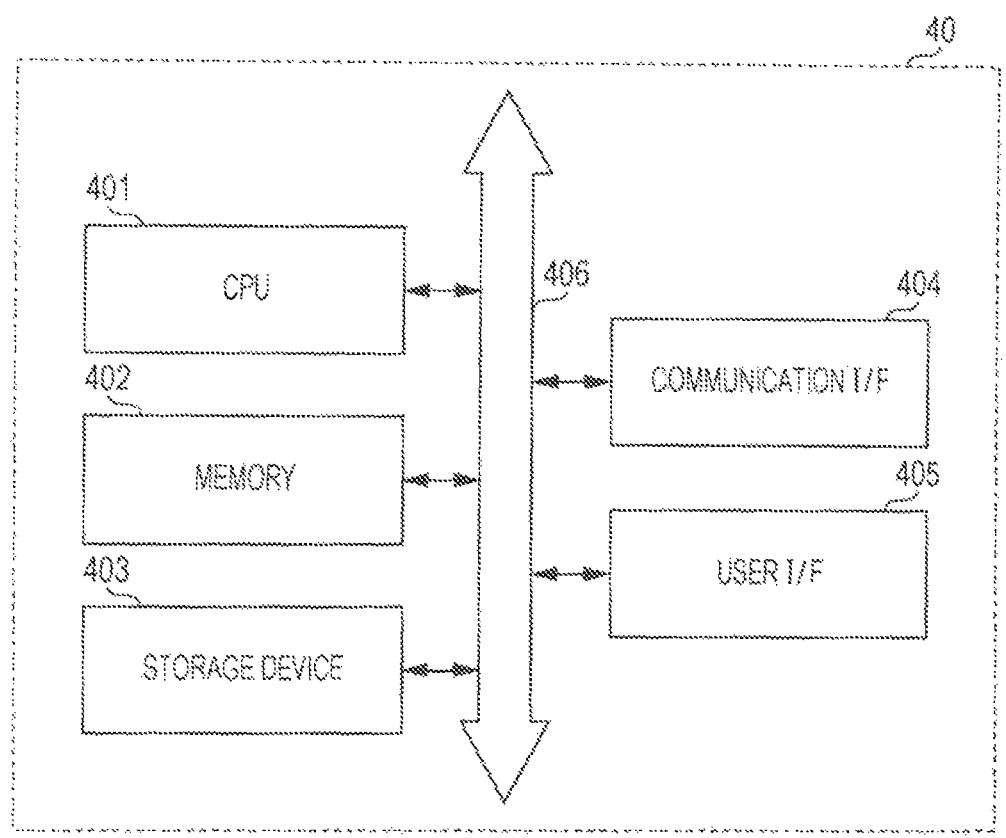
FIG. 4 is a hardware configuration diagram of a control server 40 according to an exemplary embodiment.

Next, the control server 40 according to the present exemplary embodiment will be described with reference to FIGS. 4 and 5. FIG. 4 is a hardware configuration diagram of the control server 40. As illustrated in FIG. 4, the control server 40 is provided with a CPU 401, memory 402, a storage device 403, a communication interface 404, and a user interface 405, which are respectively connected to a control bus 406. The CPU 401 centrally controls the operation of each component of the control server 40 on the basis of a control program stored in the storage device 403. The memory 402 stores position information about the user 70 transmitted from the environmental sensors 30, position information about the interactive robot 20 and external information about the user 70 transmitted from the interactive robot 20, and biological information about the user 70 transmitted from the biosensor 80 attached to the user 70.

The storage device 403 is a device such as a hard disk drive (HDD) or a solid-state drive (SSD), and stores a control program for controlling the control server 40. Additionally, although discussed later, the storage device 403 also stores a learning model used when the control server 40 estimates the emotion of the user 70.

The communication interface 404 conducts communication control by which the control server 40 transmits and receives various types of data to and from the interactive robot 20, the environmental sensors 30, and the user 70 attached to the user 70, via the access point 60. The user interface 405 is made up of a display device, such as a liquid crystal display, and an input device, such as a keyboard or a mouse. The user interface 405 is used by an administrator to adjust the control program stored in the storage device 403 or the like.

Figure 5:
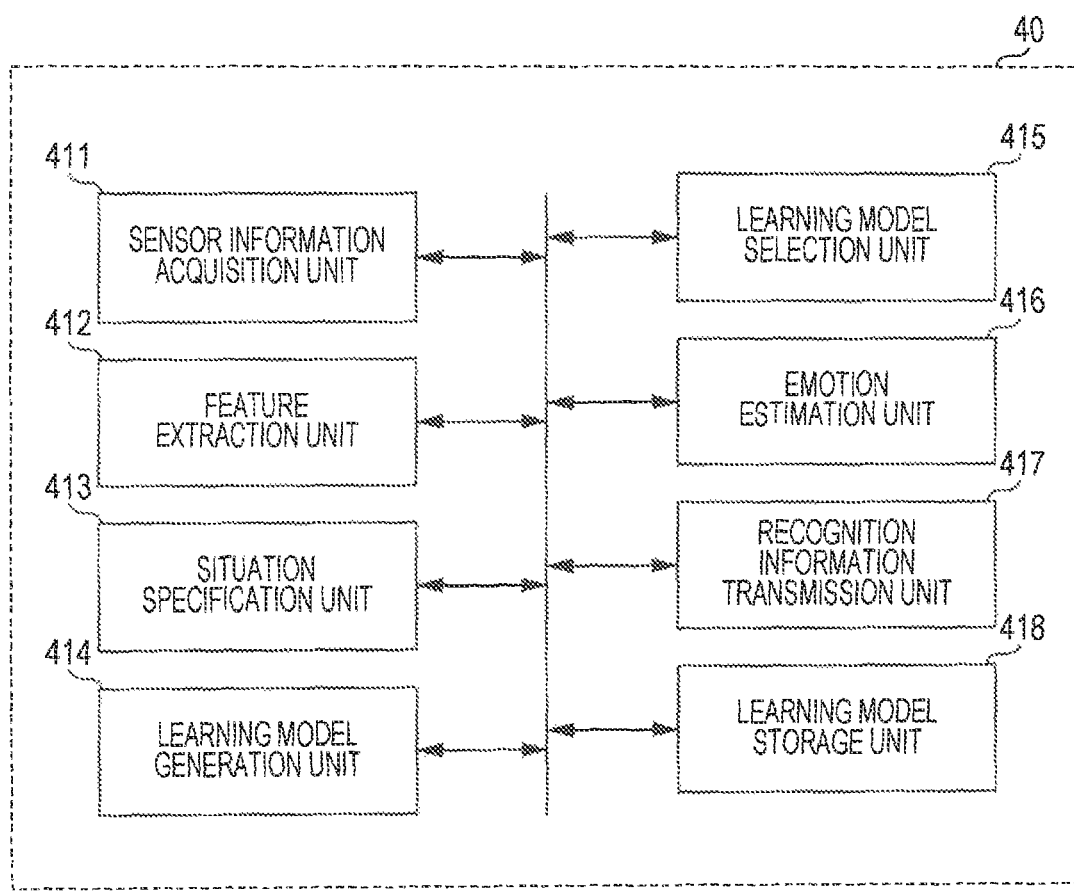
FIG. 5 is a function block diagram of a control server 40 according to an exemplary embodiment.

FIG. 5 illustrates a function block diagram of the control server 40. By having the CPU 401 execute the control program stored in the storage device 403, the control server 40 functions as a sensor information acquisition unit 411, a feature extraction unit 412, a situation specification unit 413, a learning model generation unit 414, a learning model selection unit 415, an emotion estimation unit 416, a recognition information transmission unit 417, and a learning model storage unit 418, as illustrated in FIG. 5.

The sensor information acquisition unit 411 receives external information about the user 70 transmitted from the interactive robot 20 and the environmental sensors 30, as well as biological information about the user 70 transmitted from the biosensor 80 worn by the user 70, and stores the received information in the memory 402.

From the external information and biological information acquired by the sensor information acquisition unit 411, the feature extraction unit 412 extracts features and their values used to determine the emotion of the user 70. These features may be extracted by machine learning from the acquisition of large amounts of external information and biological information by the sensor information acquisition unit 411, or may be specified by an administrator of the control server 40. For example, the features may include the expression of the user 70, or more particularly, the change compared to normal or the variation per unit time in the corners of the mouth, the change compared to normal or the variation per unit time in the pitch of the voice of the user 70, the change compared to normal or the variation per unit time in the skin potential of the user 70, and the change compared to normal or the variation per unit time in the heart rate. The value of a feature is a numerical quantification of the feature.

The situation specification unit 413 specifies the situation of the user 70, such as whether the user 70 is participating in a conference, engaged in conversation in an office, or chatting in a hallway, for example, on the basis of the current position of the user 70 and information about the current situation of the user 70 detected by the environmental sensors 30, and information about the current position of the user 70 acquired by the current position detecting device 219 of the interactive robot 20. Additionally, the situation specification unit 413 may also be configured to determine whether the specified situation is a public situation or a situation that tends to induce nervousness or stress, or alternatively, a private situation or a situation that tends to induce relaxation or relief. Furthermore, the situation specification unit 413 determines whether the natural personality of the user 70 is a type in which emotion is readily exhibited in expression and behavior, or a type in which emotion is not readily exhibited in expression and behavior.

The learning model generation unit 414 acquires large amounts of external information and biological information about the user 70 from the sensor information acquisition unit 411, and conducts machine learning to thereby generate a characteristic learning model for each emotion according to the features extracted by the feature extraction unit 412. Herein, a learning model is a definition associating a specific region containing multiple values determined by at least two features with a specific emotion. Furthermore, the learning model is also taken to include a process that, when a certain value determined by at least two features is input, determines whether or not that value is included in the specific region above, and thereby determines whether or not the value applies to the specific emotion above. For example, on a two-dimensional plane expressed by taking one feature based on external information about the user 70 as the horizontal axis and by taking one feature based on biological information about the user 70 as the vertical axis, if a certain feature acquired by the sensor information acquisition unit 411 exists inside a region specified by the curve of a certain function, the user 70 is defined to be in the state of a certain emotion. The defining of emotions may be conducted by machine learning using teaching data, or by some other method. Additionally, machine learning may also be conducted until a unique emotion is defined for a region specified by the curve of a certain function. The generated learning model is stored in the learning model storage unit 418. The learning model generation unit 414 may also generate a different learning model for individual situations of the user 70 specified by the situation specification unit 413. Additionally, a different learning model may also be generated for each user 70. Obviously, a different learning model may also be generated for each user 70 and each situation of the user 70.

The learning model selection unit 415 references the learning model storage unit 418 and selects a learning model to apply, in accordance with the current situation of the user 70 specified by the situation specification unit 413.

The emotion estimation unit 416 varies the weighting of the external information and the weighting of the biological information according to the current situation of the user 70 specified by the situation specification unit 413, on the basis of the external information and the biological information of the user 70 acquired by the sensor information acquisition unit 411, and in addition, applies the learning model selected by the learning model selection unit 415, and thereby estimates the current emotion of the user 70.

The recognition information transmission unit 417 transmits the emotion of the user 70 estimated by the emotion estimation unit 416 to the interactive robot 20 via the access point 60. The learning model storage unit 418 stores the learning model for each situation of the user 70 generated by the learning model generation unit 414.

Figure 6:
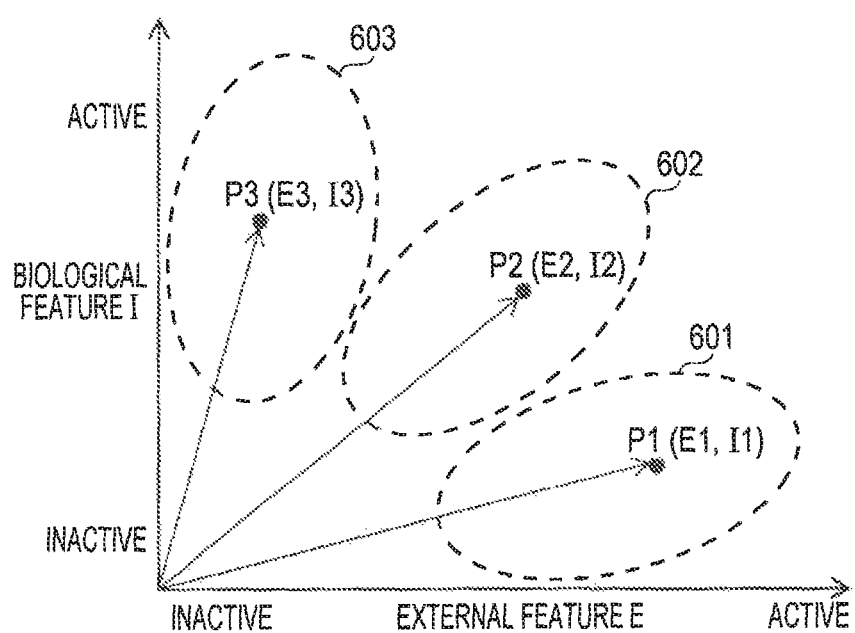
FIG. 6 is a conceptual diagram of a learning model generated for each environment around a user 70.

At this point, the learning model generated by the learning model generation unit 414 and stored in the learning model storage unit 418 will be described with reference to FIGS. 6 and 7. FIG. 6 is a conceptual diagram of a learning model generated for each environment around the user 70. In the learning model illustrated in FIG. 6, the horizontal axis represents a feature E of external information, while the vertical axis represents a feature I of biological information. The feature constituting the external information is actually made up of multiple elements, such as expression and pitch, and likewise the feature constituting the biological information is actually made up of multiple elements, such as skin potential and heart rate. Consequently, since the actual learning model is difficult is illustrate with a two-dimensional drawing as illustrated in FIG. 6, in the present exemplary embodiment, the learning model is expressed in a simplified manner with a two-dimensional drawing for the sake of simplicity.

In the learning model of FIG. 6, for example, a first region 601 is defined to be "positive", a second region 602 is defined to be "normal", and a third region 603 is defined to be "negative". At this point, if a value E1 of the feature of the external information and a value I1 of the feature of the biological information are input into the learning model, an emotion P1 of the user 70 expressed by a vector made up of the value of the feature of the external information and the value of the feature of the biological information is included inside the first region 601, and thus the emotion of the user 70 is estimated to be "positive". Similarly, if a value E2 of the feature of the external information and a value I2 of the feature of the biological information are input into the learning model, the emotion of the user 70 is estimated to be "normal", whereas if a value E3 of the feature of the external information and a value I3 of the feature of the biological information are input into the learning model, the emotion of the user 70 is estimated to be "negative". Also, the regions 601 to 603 in the learning model of FIG. 6 respectively correspond to a region specified by the curve of a certain function generated by the learning model generation unit 414. In the case in which machine learning is conducted until a unique emotion is defined for respective regions, for example, the regions 601 to 603 do not overlap with each other on the two-dimensional plane expressed by the axis based on the external information and the axis based on the biological information of the user 70, as illustrated in FIG. 6. Since the regions do not overlap with each other, a predefined emotion is specified uniquely with respect to the input of external information and biological information about the user 70.

Note that the learning model in FIG. 6 is generated for each environment around the user 70, and the learning model selection unit 415 discussed earlier selects the learning model into which to input a value of the feature of the external information and a value of the feature of the biological information, in accordance with the environment around the user 70.

Figure 7:
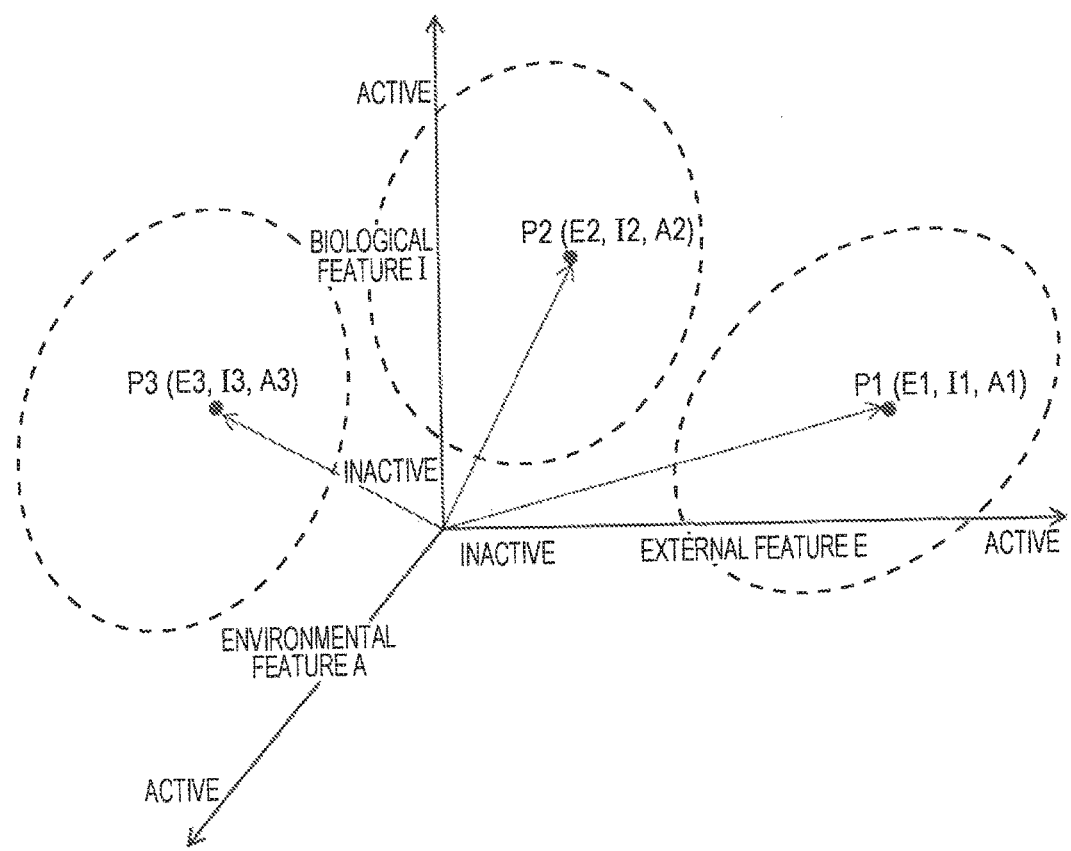
FIG. 7 is a conceptual diagram of a learning model in a case of inputting external information, biological information, and environmental information for a user 70.

FIG. 7 is a conceptual diagram of a learning model in a case of inputting external information, biological information, and environmental information for a user 70. The learning model in FIG. 7 is expressed in a three-dimensional space by adding a value of a feature of environmental information about the environment around the user 70 as a third axis to the learning model expressed in two dimensions described in FIG. 6. In this learning model, certain regions of the three-dimensional space expressed by the feature E of the external information, the feature I of the biological information, and the feature A of the environmental information are defined to be "positive", "normal", and "negative", respectively. When a value of the feature of the external information, a value of the feature of the biological information, and a value of the feature of the environmental information (for example, E1, I1, A1) are input into the learning model, the emotion estimation unit 416 determines which region corresponds to an emotion of the user 70 expressed by the vector P1 made up of those values, and outputs the corresponding emotion.

Figure 8:
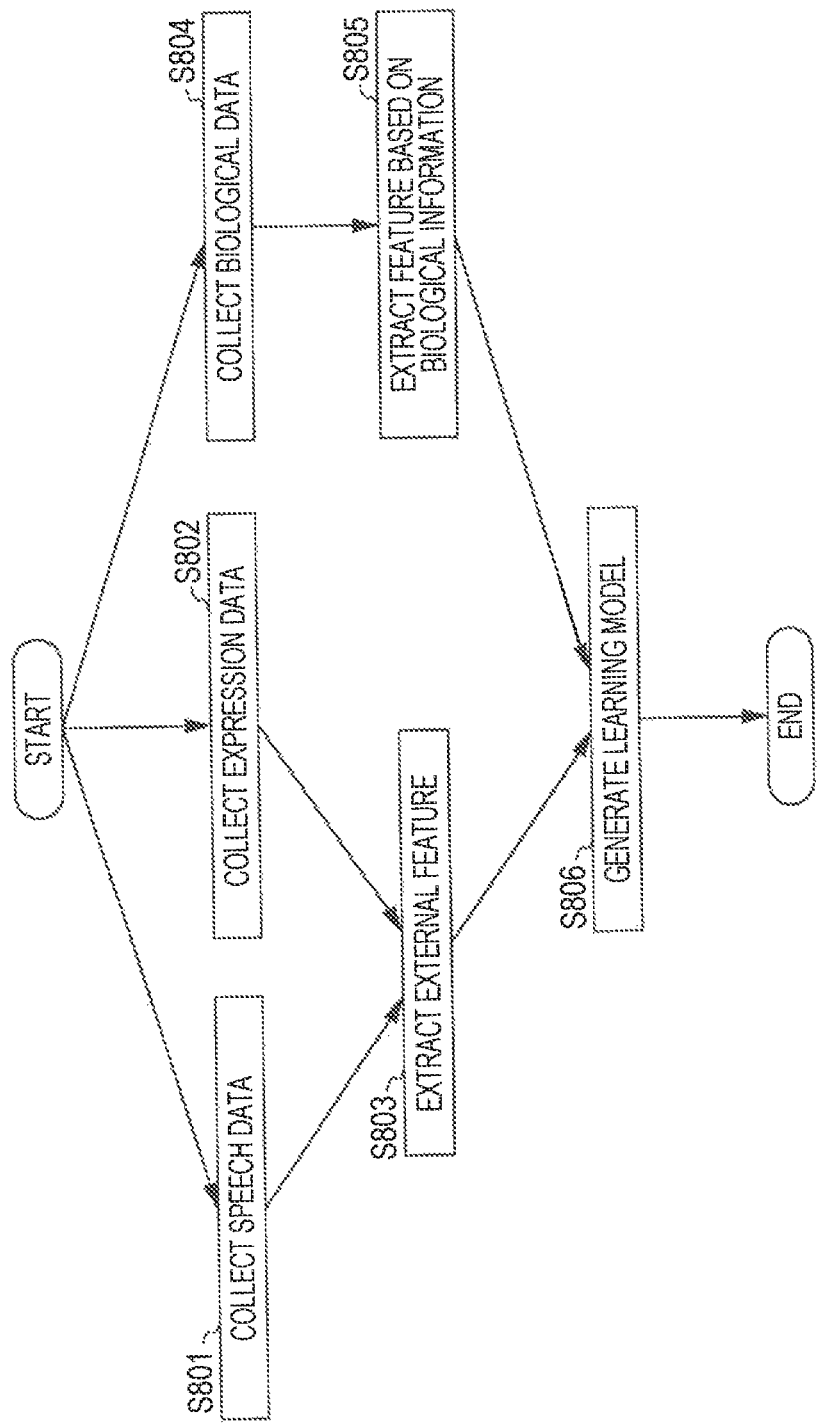
FIG. 8 is a flowchart illustrating a flow of a learning model creation process in an emotion estimating system 10 according to an exemplary embodiment.

Next, a learning model creation process by the emotion estimating system 10 will be described with reference to FIG. 8. FIG. 8 is a flowchart illustrating a flow of a learning model creation process in the emotion estimating system 10 according to the present exemplary embodiment. In step S801, the microphone 216 of the interactive robot 20 detects the speech of the user 70, and the sensor information transmission unit 221 transmits the detected speech data to the control server 40. The speech data transmitted to the control server 40 may be data converted into a digital signal by sampling the speech of the user 70, or data related to the pitch and speed of the words. The sensor information acquisition unit 411 of the control server 40 stores the speech data received from the interactive robot 20 in the memory 402, and the flow proceeds to step S803.

In step S802, which is conducted in parallel with step S801, the camera 215 of the interactive robot 20 captures the expression and behavior of the user 70, and the sensor information transmission unit 221 transmits the captured data to the control server 40. The captured data transmitted to the control server 40 may be a face image or a body image of the user 70, or may be information obtained by analyzing a face image, such as information about changes in the corners of the mouth and the angle of the eyebrows. In addition to the camera 215 of the interactive robot 20, the environmental sensors 30 may also capture the expression and behavior of the user 70, and transmit the captured data to the control server 40. The sensor information acquisition unit 411 of the control server 40 stores the image data received from the interactive robot 20 and the environmental sensors 30, and the flow proceeds to step S803.

In step S803, the feature extraction unit 412 of the control server 40 extracts a feature for determining the emotion of the user 70 from the external information acquired by the sensor information acquisition unit 411, namely the data about the expression and behavior of the user 70 captured by the interactive robot 20 and the environmental sensors 30, and the speech data of the user 70 detected by the interactive robot 20. This feature may be extracted by machine learning from the acquisition of large amounts of external information, or may be consciously decidedly by an administrator of the control server 40. The extracted feature of the external information is, for example, the change compared to normal or the variation per unit time in the corners of the mouth, the change compared to normal or the variation per unit time in the pitch of the voice of the user 70. The process subsequently proceeds to step S806.

In step S804, which is conducted in parallel with steps S801 to S803, the biosensor 80 worn by the user 70 detects biological information about the user 70. The biological information is, for example, the skin resistance value, heart rate, and body temperature of the user 70. The detected biological information is transmitted to the control server 40. The sensor information acquisition unit 411 of the control server 40 stores the speech data received from the biosensor 80 in the memory 402, and the flow proceeds to step S805.

In step S805, the feature extraction unit 412 of the control server 40 extracts a feature for determining the emotion of the user 70 from the biological information acquired by the sensor information acquisition unit 411, namely the biological data such as the skin resistance value, heart rate, and body temperature of the user 70 detected by the biosensor 80. This feature may be extracted by machine learning from the acquisition of large amounts of biological information, or may be consciously decidedly by an administrator of the control server 40. The extracted feature of the biological information is, for example, changes in the skin resistance value compared to normal, or changes in the heart rate compared to normal. The process subsequently proceeds to step S806.

In step S806, the learning model generation unit 414 of the control server 40 acquires large amounts of external information and biological information about the user 70 from the sensor information acquisition unit 411, and conducts machine learning to thereby generate a characteristic learning model for each emotion according to the features extracted by the feature extraction unit 412. The generated learning models are stored in the learning model storage unit 418, and the process ends. The learning model generation unit 414 may also generate a different learning model for individual situations of the user 70 specified by the situation specification unit 413.

Figure 9:
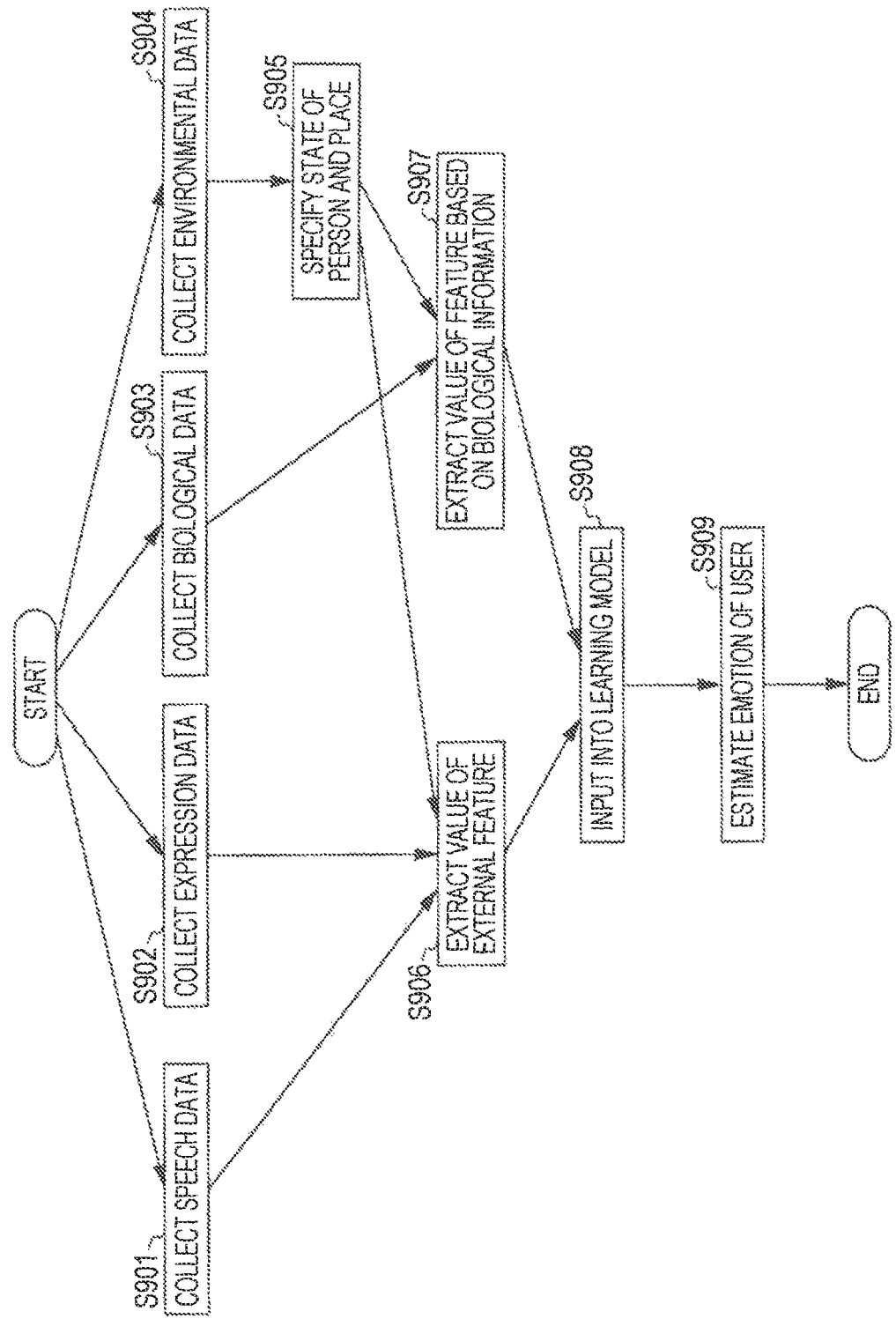
FIG. 9 is a flowchart illustrating an example of an emotion estimation process in an emotion estimating system 10 according to an exemplary embodiment.

Next, an example of a process of estimating the emotion of the user 70 in the emotion estimating system 10 according to the present exemplary embodiment will be described with reference to FIG. 9. FIG. 9 is a flowchart illustrating an example of an emotion estimation process in the emotion estimating system 10 according to the present exemplary embodiment. In step S901, the microphone 216 of the interactive robot 20 detects the speech of the user 70, and the sensor information transmission unit 221 transmits the detected speech data to the control server 40. The sensor information acquisition unit 411 of the control server 40 stores the received speech data in the memory 402, and the flow proceeds to step S906.

In step S902, which is conducted in parallel with step S901, the camera 215 of the interactive robot 20 captures the expression and behavior of the user 70, and the sensor information transmission unit 221 transmits the captured data to the control server 40. The sensor information acquisition unit 411 of the control server 40 stores the received image data in the memory 402, and the flow proceeds to step S906.

In step S903, which is conducted in parallel with steps S901 and S902, the biosensor 80 worn by the user 70 detects biological information about the user 70. The biological information is, for example, the skin resistance value, heart rate, and body temperature of the user 70. The detected biological information is transmitted to the control server 40. The sensor information acquisition unit 411 of the control server 40 stores the received biological information in the memory 402, and the flow proceeds to step S907.

In step S904, which is conducted in parallel with steps S901 to S903, the environmental sensors 30 detect information about the situation of the user 70, and transmit this information to the control server 40. In step S905, the situation specification unit 413 of the control server 40 specifies the identity of the user 70 and the situation of the user 70, on the basis of the information about the situation of the user 70 acquired by the sensor information acquisition unit 411. Next, the flow proceeds to steps S906 and S907. The identity of the user 70, such as the name, company ID, or official position of the user 70, for example, is specified by querying a server in which information about each user is stored. Also, information such as the personality type of the user 70 may also be specified. For example, information indicating whether the user 70 has a personality type in which emotion is readily exhibited in expression and behavior, or a personality type in which emotion is not readily exhibited in expression and behavior, may be specified. The situation of the user 70 is, for example, a public situation (such as a situation of talking to multiple people or a situation of participating in a conference), a private situation (such as a situation in which, other than the robot, the user is the only person in the room or nearby), a situation that tends to induce nervousness or stress (such as a situation of talking to someone in a senior position over the user 70 in the company hierarchy), or a situation that tends to induce relaxation or relief (such as a situation in which the user 70 is eating something).

For these situations, conditions for satisfying each situation are stored in the storage device 403 in advance as a table, and by referencing this table, the situation of the user 70 is specified. For example, a condition that "the user 70 is talking to multiple people" or "the user 70 is participating in a conference" is stored in the table in association with "public situation". A condition that "no one else is in the room" or "no one else is within a predetermined distance (such as a radius of 5, for example)" is stored in the table in association with "private situation". A condition that "the user 70 is talking to someone in a senior position over the user 70 in the company hierarchy" is stored in the table in association with "a situation that tends to induce nervousness or stress". Also, a condition that "the user 70 is eating something" or "the user 70 is drinking something" is stored in the table in association with "a situation that tends to induce relaxation or relief".

Subsequently, on the basis of information obtained from the sensor information acquisition unit 411, the situation specification unit 413 determines which condition in the above table is applicable, and specifies the situation associated with the condition determined to be applicable as the situation of the user 70. In the determination of which condition in the above table is applicable, the situation specification unit 413 may additionally acquire information indicating the number of people that the user 70 is talking to, who the user 70 is talking to (such as the official position, gender, age, or name), the behavior of the user 70, and the like from the sensor information acquisition unit 411, and use this information to make the determination. Note that the information related to an individual person the user 70 is talking to is acquired as follows. An individual is specified by conducting face recognition on the basis of information related to the person's face obtained from the sensor information acquisition unit 411, and information about that individual stored in the storage device 403 in advance is acquired.

In step S906, the emotion estimation unit 416 of the control server 40 computes the value of an external feature on the basis of the speech data of the user 70 and the image data of the expression and behavior of the user 70 acquired by the sensor information acquisition unit 411. At this point, the emotion estimation unit 416 applies a weight to the computed value of the external feature in accordance with the situation of the user 70 specified in step S905 above, and the flow proceeds to step S908. Note that the computed external feature may be a single value determined by a single external feature, or multiple values determined by multiple external features.

In step S907, which is conducted in parallel with step S906, the emotion estimation unit 416 of the control server 40 computes the value of a biological feature on the basis of the biological information of the user 70 acquired by the sensor information acquisition unit 411. At this point, the emotion estimation unit 416 applies a weight to the computed value of the biological feature in accordance with the situation of the user 70 specified in step S905 above, and the flow proceeds to step S908. Note that the computed biological feature may be a single value determined by a single biological feature, or multiple values determined by multiple biological features. Note that in the respective weighting of the value of the external feature and the value of the biological feature in steps S906 and S907 above, the weighting applied to the value of the biological feature is made to be larger than the weighting applied to the value of the external feature in a public situation or a situation that tends to induce nervousness or stress, for example. Conversely, the weighting applied to the value of the biological feature is made to be smaller than the weighting applied to the value of the external feature in a private situation or a situation that tends to induce relaxation or relief.

As another example, if the situation of the user 70 is specified to be a conference, the weighting applied to the value of the biological feature is made to be larger than the weighting applied to the value of the external feature. Conversely, if the situation of the user 70 is specified to be having a conversation in an office or chatting in a hallway, the weighting applied to the value of the biological feature is made to be smaller than the weighting applied to the value of the external feature.

In addition, the emotion estimation unit 416 may also change the weighting applied to the value of the external feature and the value of the biological feature in accordance with the specified personality type of the user 70. For example, if the personality of the user 70 is specified to be a type in which emotion is not readily exhibited in expression and behavior, the weighting applied to the value of the biological feature is made to be larger than the weighting applied to the value of the external feature. Conversely, if the personality of the user 70 is specified to be a type in which emotion is readily exhibited in expression and behavior, the weighting applied to the value of the biological feature is made to be smaller than the weighting applied to the value of the external feature.

In step S908, the emotion estimation unit 416 inputs the value of the external feature and the value of the biological feature computed in steps S906 and S907 above into the learning model stored in the learning model storage unit 418. Subsequently, in step S909, the emotion estimation unit 416 estimates the emotion output from the learning model as the emotion of the user. The estimated emotion is transmitted to the interactive robot 20 by the recognition information transmission unit 417. The recognition information reception unit 224 of the interactive robot 20 receives the information about the emotion of the user 70 transmitted from the control server 40, the dialogue control unit 222 modifies the dialogue content and dialogue method to match the emotion and conduct a dialogue with the user 70, and the process ends.

Figure 10:
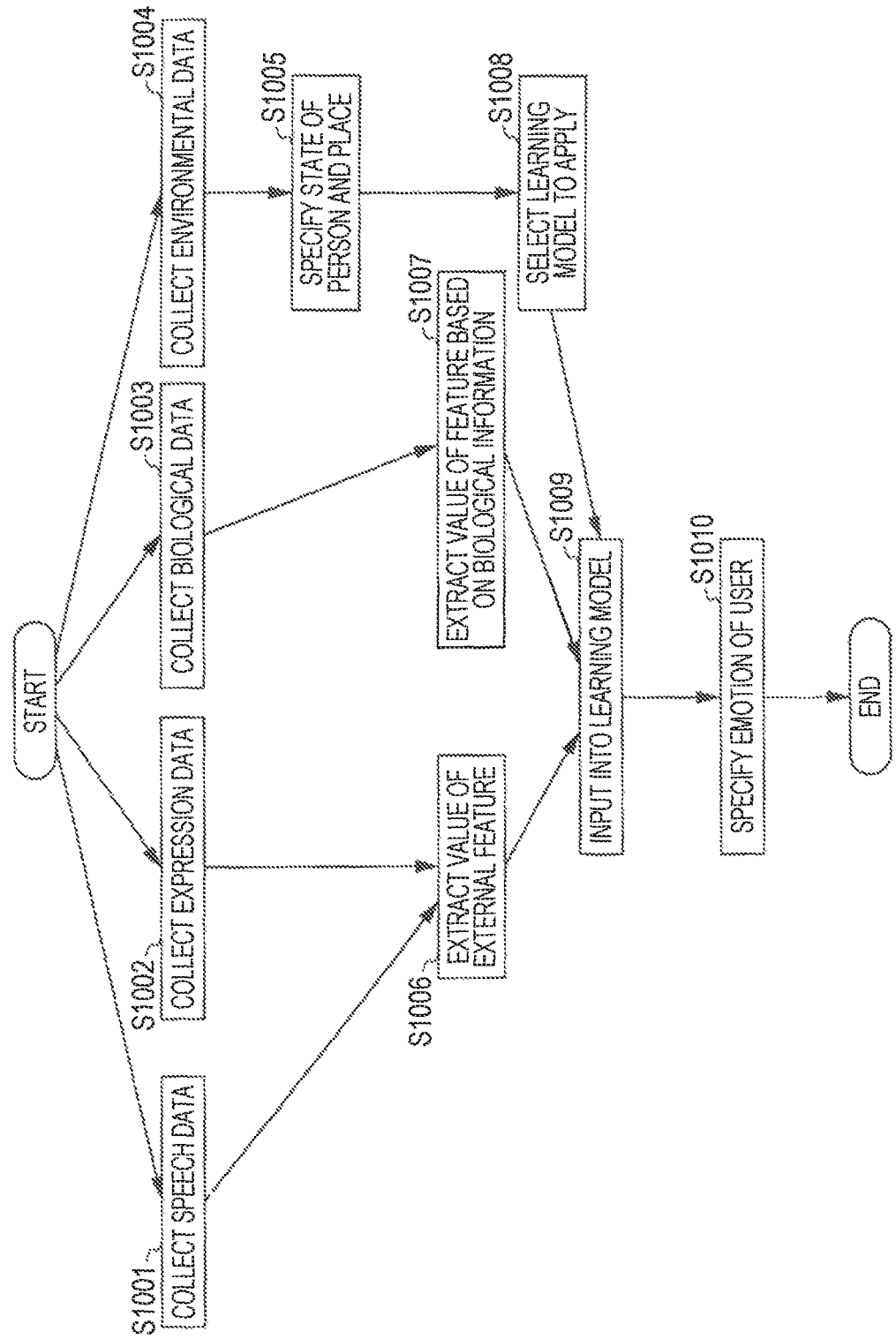
FIG. 10 is a flowchart illustrating an example of an emotion estimation process in an emotion estimating system 10 according to an exemplary embodiment.

Next, another example of a process of estimating the emotion of the user 70 in the emotion estimating system 10 according to the present exemplary embodiment will be described with reference to FIG. 10. FIG. 10 is a flowchart illustrating another example of an emotion estimation process in the emotion estimating system 10 according to the present exemplary embodiment. Note that the process from steps S1001 to S1005 in the emotion estimation process of FIG. 10 is the same as the process from steps S901 to S905 in the emotion estimation process of FIG. 9, and thus description thereof will be reduced or omitted.

In step S1006, the emotion estimation unit 416 of the control server 40 computes the value of an external feature on the basis of the speech data of the user 70 and the image data of the expression and behavior of the user 70 acquired by the sensor information acquisition unit 411. Note that the computed external feature may be a single value determined by a single external feature, or multiple values determined by multiple external features. The process subsequently proceeds to step S1009.

In step S1007, which is conducted in parallel with step S1006, the emotion estimation unit 416 of the control server 40 computes the value of a biological feature on the basis of the biological information of the user 70 acquired by the sensor information acquisition unit 411. Note that the computed biological feature may be a single value determined by a single biological feature, or multiple values determined by multiple biological features. The process subsequently proceeds to step S1009.

Also, in step S1008, which is conducted next after step S1005, the learning model selection unit 415 selects a learning model to use from among multiple learning models stored in the learning model storage unit 418, in accordance with factors such as the situation of the user 70 estimated in step S1005, the particular user 70, or the personality type of the user 70. The flow then proceeds to step S1009.

In step S1009, the emotion estimation unit 416 inputs the value of the external feature and the value of the biological feature computed in steps S1006 and S1007 above into the learning model stored in the learning model storage unit 418.

In step S1010, the emotion estimation unit 416 estimates the emotion output from the learning model as the emotion of the user. The estimated emotion is transmitted to the interactive robot 20 by the recognition information transmission unit 417. The recognition information reception unit 224 of the interactive robot 20 receives the information about the emotion of the user 70 transmitted from the control server 40, the dialogue control unit 222 modifies the dialogue content and dialogue method to match the emotion and conduct a dialogue with the user 70, and the process ends.

Figure 11:
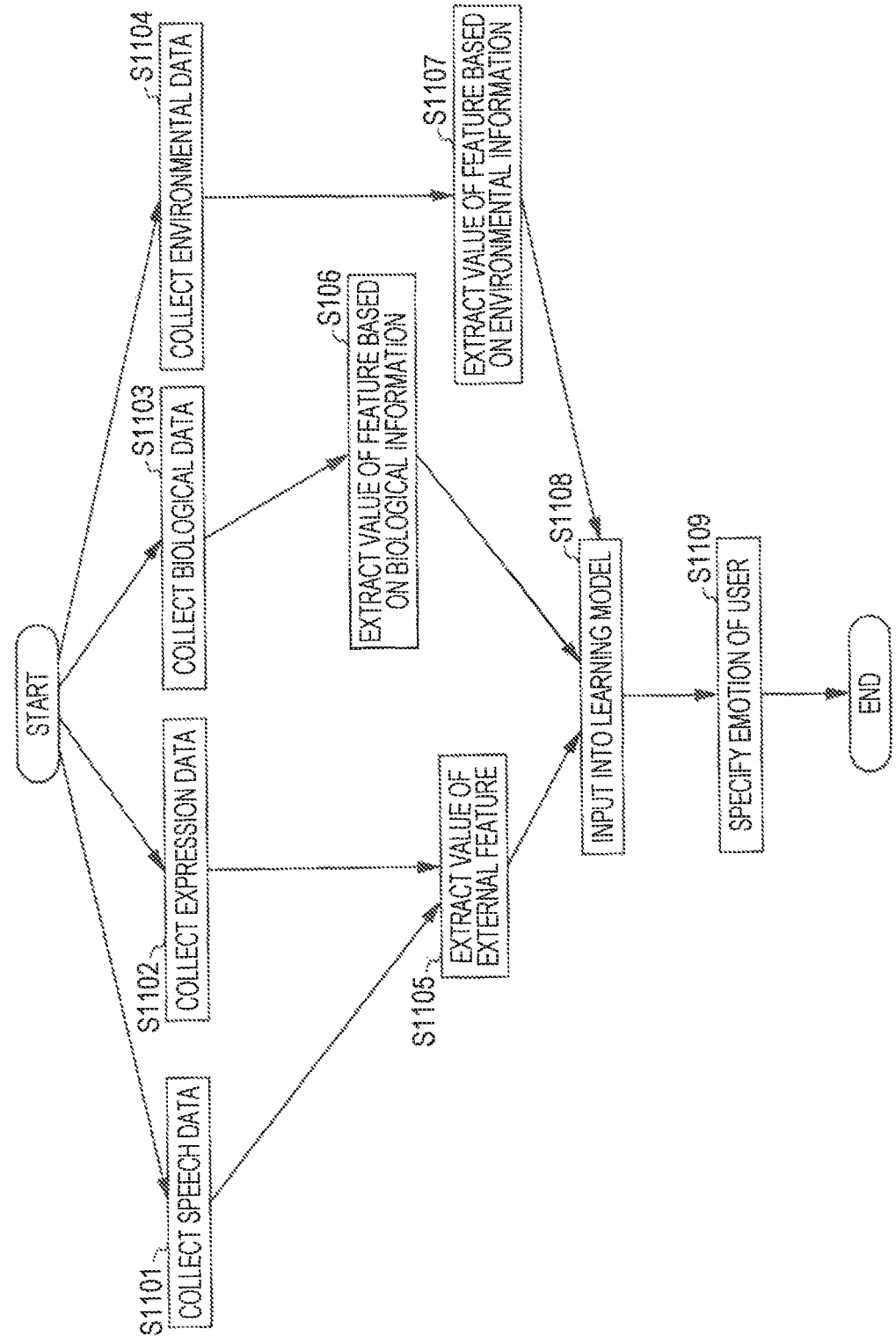
FIG. 11 is a flowchart illustrating another example of an emotion estimation process in an emotion estimating system 10 according to an exemplary embodiment.

Note that above examples describe a case of computing the values of respective features for external information and biological information, and weighting the respective values in accordance with the situation of the user 70, or applying a learning model depending on the situation of the user 70. However, the values of respective features for external information and biological information as well as environmental information, or in other words the situation of the user 70, may also be computed, a vector corresponding to these three elements may be computed, and a certain learning model may be applied to estimate the emotion of the user 70 that corresponds to the vector in the learning model. The flow of the process in this case will be described with reference to FIG. 11. FIG. 11 is a flowchart illustrating another example of an emotion estimation process in the emotion estimating system 10 according to the present exemplary embodiment.

The process from steps S1101 to S1104 in the emotion estimation process of FIG. 11 is the same as the process from steps S901 to S904 in the emotion estimation process of FIG. 9, and thus description thereof will be reduced or omitted. In step S1105, the emotion estimation unit 416 of the control server 40 computes the value of an external feature on the basis of the speech data of the user 70 and the image data of the expression and behavior of the user 70 acquired by the sensor information acquisition unit 411, and the flow proceeds to step S1108. In step S1106, which is conducted in parallel with step S1105, the emotion estimation unit 416 of the control server 40 computes the value of a biological feature on the basis of the biological information of the user 70 acquired by the sensor information acquisition unit 411, and the flow proceeds to step S1108.

In step S1107, which is conducted in parallel with steps S1105 and S1106, the situation specification unit 413 of the control server 40 computes the value of an environmental feature on the basis of the environmental information about the environment around the user 70 acquired by the sensor information acquisition unit 411, and the flow proceeds to step S1108. In step S1108, the emotion estimation unit 416 inputs the value of the external feature, the value of the biological feature, and the value of the environmental feature computed in steps S1105 to S1107 above into the learning model stored in the learning model storage unit 418. Subsequently, in step S1109, the emotion estimation unit 416 estimates the emotion output from the learning model as the emotion of the user. The estimated emotion is transmitted to the interactive robot 20 by the recognition information transmission unit 417. The recognition information reception unit 224 of the interactive robot 20 receives the information about the emotion of the user 70 transmitted from the control server 40, the dialogue control unit 222 modifies the dialogue content and dialogue method to match the emotion and conduct a dialogue with the user 70, and the process ends.

Note that the learning model used in the above example is one that outputs an emotion of the user 70 when a feature of external information, a feature of biological information, and a feature of environmental information are input, as illustrated in FIG. 7.

[Exemplary Modifications]

The above example thus describes an example of estimating the emotion of the user 70 in the control server 40, but the present invention is not limited to a method in which the control server 40 estimates the emotion of the user 70, and by taking a configuration in which the interactive robot 20 is provided with the respective components of the present exemplary embodiment, the interactive robot 20 may be configured to estimate the emotion of the user 70.

In this case, the interactive robot 20 moves to the location of the user 70 and acquires biological information and external information about the user 70, on the basis of an image of the user 70 captured by the camera 215 and speech of the user 70 detected by the microphone 216. The biological information includes information about the heart rate and body temperature of the user 70, for example, while the external information includes information about the expression of the user 70, for example. In addition, the interactive robot 20 acquires information about the situation of the user 70 from the environmental sensors 30 installed near the movement destination.

At this point, in order to acquire information about the situation of the user 70 from the environmental sensors 30, it may be configured so that the interactive robot 20 transmits position information about the movement destination of the interactive robot 20 detected by the current position detecting device 219 of the interactive robot 20 to the control server 40, and the control server 40 replies to the interactive robot 20 with information detected by the environmental sensors 30 corresponding to the position information, for example. If information corresponding to the position information is not acquired in the control server 40, the control server 40 drives the environmental sensors 30 existing near the position specified by the position information (in other words, the control server 40 instructs the relevant environmental sensors 30 to acquire environmental information), and thereby causes the environmental sensors 30 to detect information about the situation of the user 70. After the detected information is acquired by the control server 40, the detected information is transmitted to the interactive robot 20.

The interactive robot 20 computes the value of the external feature on the basis of the acquired external information, computes the value of the biological feature on the basis of the acquired biological information, applies a weight to each value on the basis of the information about the situation of the user 70, inputs the weighted values into the learning model, and thereby estimates the emotion of the user 70. Alternatively, the interactive robot 20 selects a learning model to apply on the basis of the information about the situation of the user 70, inputs the value of the external feature and the value of the biological feature into the selected learning model, and thereby estimates the emotion of the user 70. Alternatively, the interactive robot 20 computes the value of a feature based on the environmental information, on the basis of the information about the situation of the user 70, inputs the computed value, the value of the external feature, and the value of the biological feature into the learning model, and thereby estimates the emotion of the user 70.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An emotion estimating system, comprising:
   a learning model configured to accept external information and biological information as input, and configured to output a determination of an emotion of a user based on the external information and the biological information; and
   an estimation unit configured to:
      receive the external information about the user detected by a first detector and the biological information about the user detected by a second detector,
      determine a weighting factor for the external information and a weighting factor for the biological information based on a situation around the user, and
      estimate an emotional state of the user by inputting the weighted external information and the weighted biological information into the learning model.

2. The emotion estimating system according to claim 1, wherein
   the situation around the user is determined on a basis of environment information detected by a third detector that detects environmental information about an environment around the user.

3. The emotion estimating system according to claim 2, wherein
   when the estimation unit determines that the situation around the user is a public situation or a situation that tends to induce nervousness or stress, the estimation unit makes the weighting factor for the biological information larger than the weighting factor for the external information.

4. The emotion estimating system according to claim 2, wherein
   when the estimation unit determines that the situation around the user is a private situation or a situation that tends to induce relaxation or relief, the estimation unit makes the weighting factor for the biological information smaller than the weighting factor for the external information.

5. The emotion estimation system according claim 1, wherein
   when the estimation unit determines that the user has a personality type in which emotion is not readily exhibited in expression and behavior, the estimation unit makes the weighting factor for the biological information larger than the weighting factor for the external information.

6. The emotion estimating system according to claim 1, wherein
   when the estimation unit determines that the user has a personality type in which emotion is readily exhibited in expression and behavior, the estimation unit makes the weighting factor for the biological information smaller than the weighting factor for the external information.

7. An emotion estimating system, comprising:
   a plurality of learning models, each of which is configured to accept external information and biological information as input, and configured to output a determination of an emotion of a user based on the external information and the biological information;
   a selector that selects a learning model to use, in accordance with a situation around the user; and
   an estimation unit configured to:
      receive the external information about the user detected by a first detector and the biological information about the user detected by a second detector, and
      estimate an emotional state of the user by inputting the external information and the biological information into the selected learning model.

8. The emotion estimating system according to claim 7, further comprising:
   a third detector that detects environmental information about an environment around the user, wherein
   the selector determines the situation around the user on a basis of the environmental information detected by the third detector.

9. An emotion estimating system, comprising:
   a learning model that is configured to accept external information, biological information, and environmental information about an environment around a user as input, and configured to output an emotion of the user based on the external information, the biological information, and the environmental information; and
   an estimation unit configured to:
      receive the external information about the user detected by a first detector, the biological information about the user detected by a second detector, and the environmental information about the environment around the user detected by a third detector, and
      estimate an emotional state of the user by inputting the external information, the biological information, and the environmental information into the learning model.

10. The emotion estimating system according to claim 1, wherein
   the first detector detects at least one of an expression and speech of the user as the external information, and the second detector detects at least one of skin potential and heart rate of the user as the biological information.

11. The emotion estimating system according to claim 1, wherein
the first detector and the second detector are provided in an interactive robot.

12. The emotion estimating system according to claim 11, wherein
environmental information about an environment around the user is detected by an environmental sensor installed near where the interactive robot is present.

13. The emotion estimating system according to claim 12, wherein
the emotion estimating system includes a control server,
the interactive robot transmits current position information to the control server, and
the control server transmits, to the interactive robot, environmental information about the environment around the user acquired from an environmental sensor installed at a position corresponding to the current position information acquired from the interactive robot.

14. The emotion estimating system according to claim 13, wherein
the control server requests the environmental sensor installed at a position corresponding to the current position information acquired from the interactive robot to acquire the environmental information about the environment around the user.

* * * * *